United States Patent
Sasaki (10) Patent No.: US 12,138,376 B2
(45) Date of Patent: Nov. 12, 2024

(54) LIGHT IRRADIATION DEVICE

(71) Applicant: TERUMO KABUSHIKI KAISHA, Tokyo (JP)

(72) Inventor: Michihiro Sasaki, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 749 days.

(21) Appl. No.: 17/347,826

(22) Filed: Jun. 15, 2021

(65) Prior Publication Data
US 2021/0308360 A1 Oct. 7, 2021

Related U.S. Application Data (63) Continuation of application No. 16/086,989, filed as application No. PCT/JP2017/011326 on Mar. 22, 2017, now abandoned.

(30) Foreign Application Priority Data

Mar. 23, 2016 (JP) .................. 2016-059057

(51) Int. Cl.
*A61M 1/36* (2006.01)
*A61L 2/00* (2006.01)
(52) U.S. Cl.
CPC ......... *A61M 1/3681* (2013.01); *A61L 2/0047* (2013.01); *A61M 2205/053* (2013.01)
(58) Field of Classification Search
CPC ........... A61M 1/3681; A61M 2205/053; A61L 2/0047
USPC ...................................................... 604/6.08
See application file for complete search history.

(56) References Cited

U.S. PATENT DOCUMENTS

| | | | |
|---|---|---|---|
| 2,213,403 A * | 9/1940 | Miller | A61M 15/02 128/202.25 |
| 2,254,994 A | 9/1941 | Butland | |
| 4,464,166 A | 8/1984 | Edelson | |
| 4,708,715 A * | 11/1987 | Troutner | A61M 1/3683 439/235 |
| 4,737,140 A | 4/1988 | Lee et al. | |
| 4,952,812 A | 8/1990 | Miripol et al. | |
| 5,190,766 A | 3/1993 | Ishihara | |
| 5,399,719 A | 3/1995 | Wolowitz et al. | |

(Continued)

FOREIGN PATENT DOCUMENTS

| | | |
|---|---|---|
| CN | 2162248 Y | 4/1994 |
| GB | 2200020 A | 7/1988 |

(Continued)

OTHER PUBLICATIONS

International Searching Authority, Invitation to Pay Additional Fees. PCT/2016/043759, Oct. 26, 2016, 7 pages.

(Continued)

*Primary Examiner* — Andrew J Mensh
(74) *Attorney, Agent, or Firm* — Sheridan Ross P.C.

(57) ABSTRACT

A light irradiation device includes: a flow channel through which blood or a blood component flows; and an LED lamp which irradiates the blood or the blood component flowing through the flow channel with light so as to inactivate a virus included in the blood or the blood component, in which a multilayer structure in which a plurality of the flow channels is arranged in parallel is formed.

9 Claims, 5 Drawing Sheets

(56) References Cited

U.S. PATENT DOCUMENTS

| | | | |
|---|---|---|---|
| 5,702,432 A * | 12/1997 | Chen | A61N 5/062 604/21 |
| 5,827,644 A | 10/1998 | Floyd et al. | |
| 5,868,695 A * | 2/1999 | Wolf, Jr. | A61L 2/08 604/20 |
| 6,113,566 A | 9/2000 | Schleicher | |
| 6,258,577 B1 | 7/2001 | Goodrich, Jr. et al. | |
| 6,268,120 B1 | 7/2001 | Platz et al. | |
| 6,277,337 B1 | 8/2001 | Goodrich, Jr. et al. | |
| 6,548,241 B1 | 4/2003 | McBurney et al. | |
| 6,828,323 B2 | 12/2004 | Platz et al. | |
| 7,361,427 B1 | 4/2008 | Dow et al. | |
| 7,479,123 B2 | 1/2009 | Briggs | |
| 8,057,418 B2 | 11/2011 | Korbling et al. | |
| 9,265,876 B1 | 2/2016 | Ben-Hur | |
| 9,603,989 B2 | 3/2017 | Brown | |
| 10,301,195 B2 | 5/2019 | Smetona et al. | |
| 2002/0096648 A1 * | 7/2002 | Kaiser | A23L 3/28 250/492.1 |
| 2003/0113704 A1 | 6/2003 | Stassinopoulos et al. | |
| 2003/0146162 A1 | 8/2003 | Metzel et al. | |
| 2004/0256329 A1 * | 12/2004 | Meserol | A61M 1/3681 210/205 |
| 2011/0021966 A1 * | 1/2011 | Leonard | A61M 37/00 210/748.14 |
| 2014/0097353 A1 | 4/2014 | Ben-Hur et al. | |
| 2016/0058937 A1 | 3/2016 | Gaitas et al. | |
| 2016/0354503 A1 * | 12/2016 | Hutchens | A61L 2/0047 |
| 2017/0021042 A1 | 1/2017 | Dodd et al. | |

FOREIGN PATENT DOCUMENTS

| | | |
|---|---|---|
| GB | 2200020 B | 7/1988 |
| JP | 2000/503579 A | 3/2000 |
| JP | 2005/516978 A | 6/2005 |
| JP | 2016/087071 A | 5/2016 |
| WO | 9814243 A1 | 4/1998 |
| WO | 03/063915 A1 | 8/2003 |
| WO | 2008/034476 A1 | 3/2008 |
| WO | 2009/079383 A | 6/2009 |

OTHER PUBLICATIONS

International Searching Authority, International Search Report, PCT/US2016/043759, Jan. 4, 2017, 16 pages.

International Searching Authority, International Search Report, PCT/JP2017/011326, Apr. 25, 2017, 4 pages.

European Patent Office; European Search Report, EP17770244.6, Oct. 15, 2019, 7 pages.

Liguo Zhu et al., "The Effectiveness of Riboflavin Photochemical-Mediated Virus Inactivation and Changes in Protein Retention in Fresh-Frozen Plasma Treated Using a Flow-Based Treatment Device"; Transfusion, vol. 55, Jan. 2015, 8 pages.

Reinhard Henschler, Erhard Seifried, Nina Mufti; "Development of the S-303 Pathogen Inactivation Technology for Red Blood Cell Concentrates"; Transfusion Medicine and Hemotherapy, Jan. 31, 2011, 10 pages.

State Intellectual Property of Office of People's Republic of China, First Office Action, CN201780019460.0, Aug. 4, 2020, 15 pages.

* cited by examiner

LIGHT IRRADIATION DEVICE

CROSS REFERENCE TO RELATED APPLICATIONS

The present application claims the benefit of National Stage Entry from a PCT application PCT/JP2017/011326 filed Mar. 22, 2017, and priority, under 35 U.S.C. § 119 (e), to U.S. application Ser. No. 16/086,989, filed Sep. 20, 2018, entitled "Light Irradiation Device." The entire disclosures of the applications listed above are hereby incorporated by reference, in their entirety, for all that they teach and for all purposes.

TECHNICAL FIELD

The present invention relates to a light irradiation device that irradiates blood or a blood component with light in order to inactivate a virus included in the blood or the blood component.

BACKGROUND ART

In order to take adequate measures against a virus propagating through blood, a process of inactivating a virus included in a blood product is performed on various blood products (whole blood, concentrated erythrocytes, platelets, and plasma) manufactured on the basis of blood sampled from a blood donor.

As a device configured to inactivate the virus included in such blood products, Patent Literature 1 discloses a light irradiation device that irradiates a blood bag containing blood with light.

CITATION LIST

Patent Literature

Patent Literature 1: Japanese Patent No. 4154191

SUMMARY OF INVENTION

Technical Problem

The virus is inactivated while stirring the blood in the blood bag to pass through a thin layer portion in the light irradiation device disclosed in Patent Literature 1. However, it takes a lot of time to inactivate the virus by sufficiently stirring the blood in the blood bag. Thus, the time required to inactivate the virus included in the blood in the blood bag increases.

Thus, there is a concern that blood coagulation may occur.

Therefore, the present invention has been made to solve the above-described problems, and an object thereof is to provide a light irradiation device capable of causing blood coagulation to hardly occur and inactivating a virus included in blood or a blood component in a short time.

Solution to Problem

One aspect of the present invention made to solve the above-described problems is a light irradiation device including: a flow channel through which blood or a blood component flows; and an LED lamp which irradiates the blood or the blood component flowing through the flow channel with light so as to inactivate a virus included in the blood or the blood component. In the light irradiation device, a multilayer structure in which a plurality of the flow channels is arranged in parallel is formed.

According to this aspect, it is possible to increase the total volume of the flow channels by forming the multilayer structure in which the plurality of flow channels is arranged in parallel. Thus, it is possible to increase the throughput of the blood or the blood component per unit time so that the processing performance to inactivate the virus included in the blood or the blood component is improved. In addition, the blood or the blood component is irradiated with light while causing the blood or the blood component to flow through the flow channel so that blood coagulation hardly occurs. Therefore, the blood coagulation hardly occurs, and it is possible to inactivate the virus included in the blood or the blood component in a short time.

In the above-described aspect, it is preferable that the multilayer structure be formed for each of a first direction orthogonal to an axial direction of the flow channel and a second direction orthogonal to the axial direction of the flow channel and the first direction.

According to this aspect, it is possible to further increase the throughput of the blood or the blood component per unit time. Thus, the processing performance to inactivate viruses included in the blood or the blood component is further improved so that it is possible to inactivate the virus included in the blood or the blood component in a shorter time.

In the above-described aspect, it is preferable that the LED lamp be arranged at positions on both sides with respect to the flow channel in the direction orthogonal to the axial direction of the flow channel.

According to this aspect, it is possible to increase an irradiation amount of light with respect to the blood or the blood component flowing through the flow channel. In addition, the light is easily transmitted into the blood or the blood component flowing through the flow channel. Thus, the processing performance to inactivate the virus included in the blood or the blood component is improved.

In the above-described aspect, it is preferable that a section of the flow channel perpendicular to the axial direction of the flow channel be formed in a flat shape, and that the LED lamp be arranged at a position on a side in a lateral direction of the flat shape with respect to the flow channel.

According to this aspect, the light is easily transmitted into the blood or the blood component flowing through the flow channel. Thus, the processing performance to inactivate the virus included in the blood or the blood component is improved.

In the above-described aspect, it is preferable that a plurality of the LED lamps be arranged in the axial direction of the flow channel.

According to this aspect, it is possible to increase an irradiation amount of light with respect to the blood or the blood component flowing through the flow channel. Thus, the processing performance to inactivate the virus included in the blood or the blood component is improved.

In the above-described aspect, it is preferable that the flow channel be formed in a linear shape in the axial direction of the flow channel.

According to this aspect, the blood or the blood component flowing through the flow channel hardly receives a flow channel resistance, and thus, it is possible to increase the throughput of the blood or the blood component per unit time.

In the above-described aspect, it is preferable that the flow channel be formed in a curved shape in the axial direction of the flow channel.

According to this aspect, it is possible to secure the volume of the flow channel within a limited space, and thus, it is possible to increase the throughput of the blood or the blood component per unit time.

In the above-described aspect, it is preferable that the light be ultraviolet light.

According to this aspect, it is possible to effectively inactivate the virus by the ultraviolet light, and thus, the processing performance of inactivating the virus included in the blood or the blood component is improved.

Advantageous Effects of Invention

According to the light irradiation device of the present invention, it is possible to cause the blood coagulation to hardly occur and to inactivate the virus included in the blood or the blood component in a short time.

DESCRIPTION OF EMBODIMENTS

Figure 1:
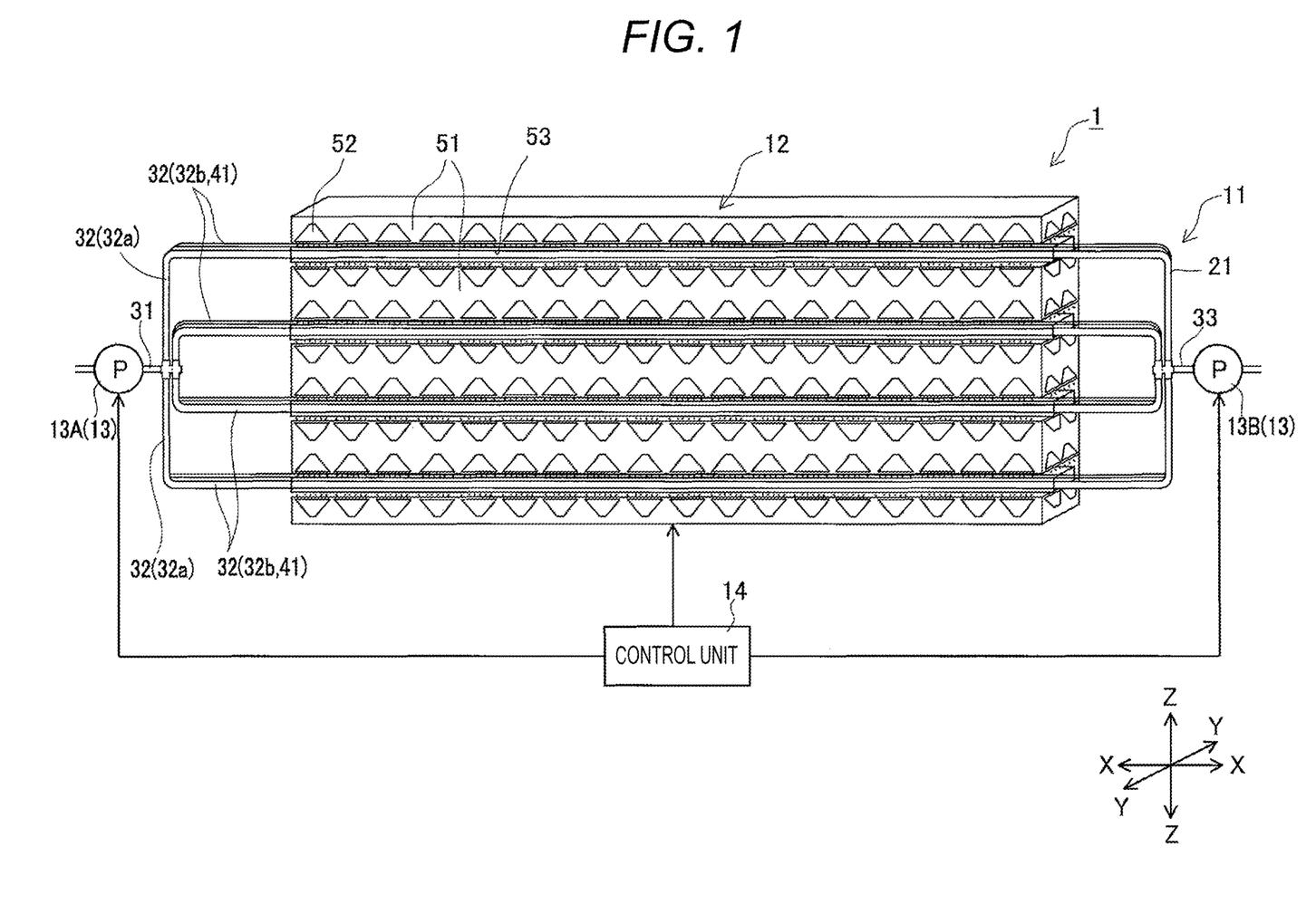
FIG. 1 is a configuration diagram of a UV irradiation unit according to the present embodiment.

First, a structure of a UV irradiation unit 1 as an example of a light irradiation device of the present invention will be described. The UV irradiation unit 1 includes a circuit unit 11, an irradiation unit 12, a feed pump 13, a control unit 14, and the like as illustrated in FIG. 1. Incidentally, XYZ axes orthogonal to each other are assumed as illustrated in FIG. 1 and the like for the convenience of description. Here, an X-axis direction is a direction (left-right direction in FIG. 1) parallel to an axial direction (an axial line direction or a center axis direction) of a second portion 32b (a flow channel 41) of a branch tube 32, and corresponds to a flow direction of blood or a blood component flowing through a flow channel 41 in the second portion 32b of the branch tube 32.

Figure 3:
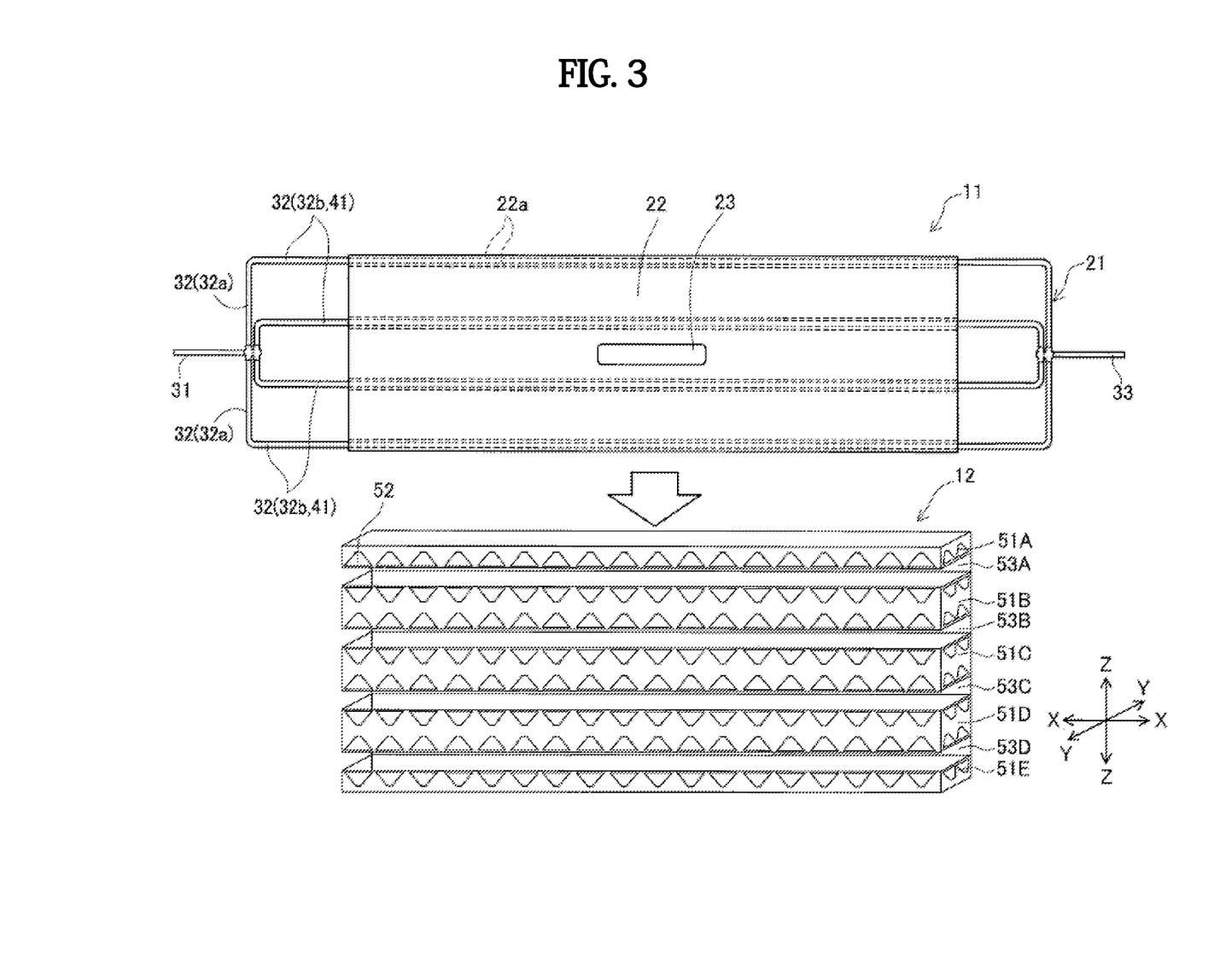
FIG. 3 is an exploded view of the UV irradiation unit of the present embodiment.

As illustrated in FIGS. 1 and 3, the circuit unit 11 includes a plurality of tubes 21, an attachment assist portion 22, and the like.

The tube 21 includes a flow channel 41 for flow of the blood or the blood component. Here, the flow channel 41 corresponds to an inner cavity of the tube 21. In addition, the blood or the blood component is whole blood or concentrated erythrocytes, platelets, or plasma, and will be collectively simply referred to as "blood" hereinafter. The tube 21 is made of a transparent resin that is disposable and does not contain a UV absorbent. As a result, it is possible to subject the blood flowing through the flow channel 41 to more UV light (ultraviolet light) emitted from a UV LED lamp 52.

The circuit unit 11 includes one inlet-side tube 31, a plurality of branch tubes 32, and one outlet-side tube 33 as the plurality of tubes 21. Further, the plurality of branch tubes 32 is connected to the inlet-side tube 31 and the outlet-side tube 33. That is, the plurality of branch tubes 32 branching from the single inlet-side tube 31 is connected to the single outlet-side tube 33 in the circuit unit 11. In this manner, the plurality of tubes 21 is integrated in the circuit unit 11.

Incidentally, the branch tube 32 has a first portion 32a whose axial direction (blood flow direction) is formed along a Z-axis direction and the second portion 32b whose axial direction is formed along the X-axis direction.

Figure 2:
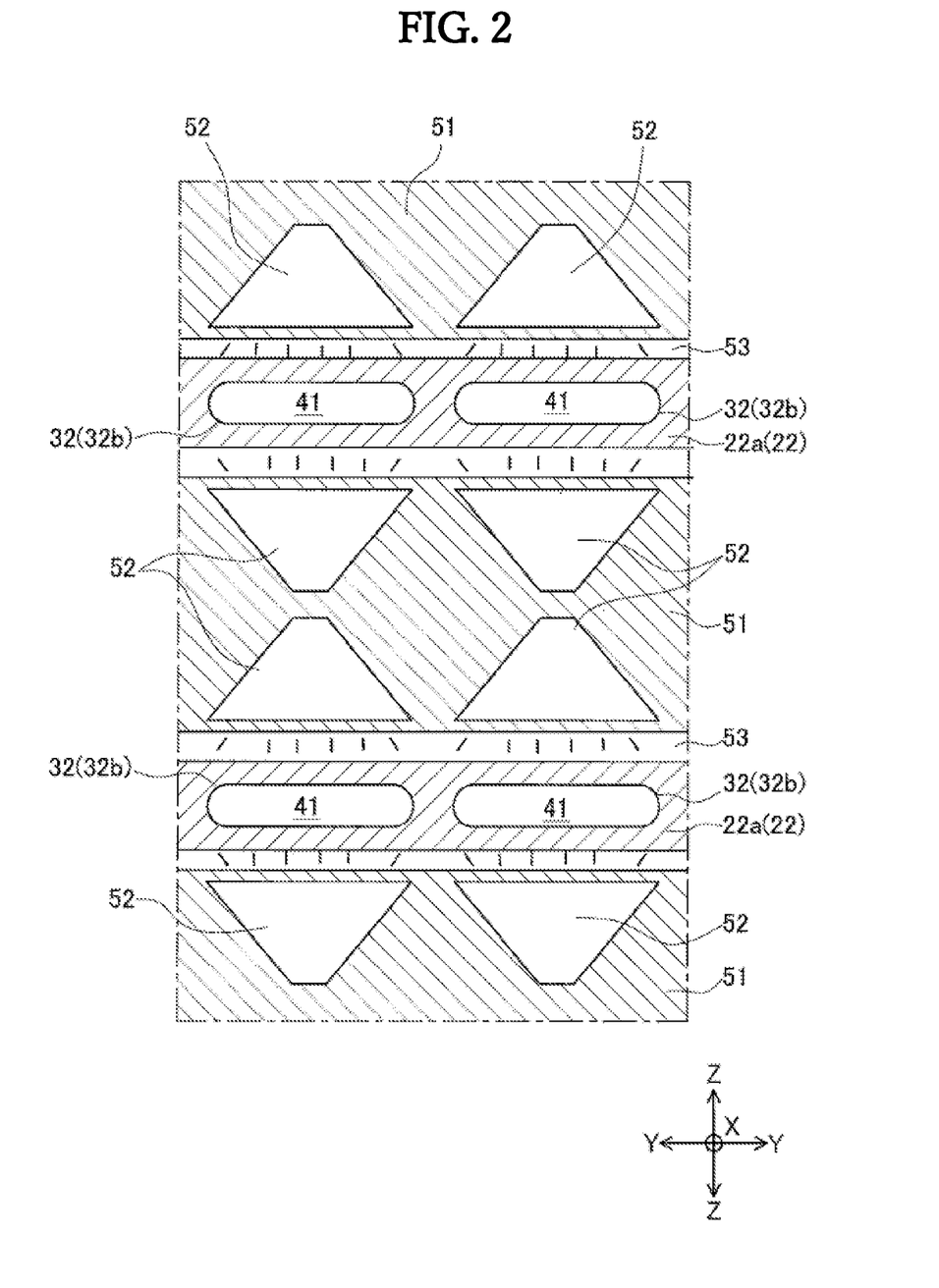
FIG. 2 is a view illustrating a YZ section of a flow channel and a peripheral portion of an ultraviolet LED lamp.

In the present embodiment, the plurality of branch tubes 32 is arranged in parallel as illustrated in FIGS. 1 to 3. In particular, the second portions 32b of the plurality of branch tubes 32 are arranged in parallel for each of a Y-axis direction (a first direction orthogonal to the axial direction (blood flow direction) of the flow channel 41) and the Z-axis direction (a second direction orthogonal to the axial direction of the flow channel 41 and the first direction). As a result, a multilayer structure in which the plurality of flow channels 41 is arranged in parallel for each of the Y-axis direction and the Z-axis direction is formed in the UV irradiation unit 1.

In addition, a flow channel section (a YZ section (a section formed in the Y-axis direction and the Z-axis direction)) of the flow channel 41 perpendicular to the axial direction of the flow channel 41 is formed in a flat shape as illustrated in FIG. 2. Specifically, the flow channel section of the flow channel 41 is formed in the flat shape having the Y-axis direction as a longitudinal direction and the Z-axis direction as a traverse direction. In the present embodiment, an outer shape of the flow channel section of the flow channel 41 is formed in, for example, an oval shape (a shape having a pair of mutually opposing linear portions and a pair of arc portions connecting both ends of the linear portions).

In addition, the second portion 32b of the branch tube 32 is formed in a linear shape along the X-axis direction as illustrated in FIG. 1. In this manner, the flow channel 41 at the second portion 32b of the branch tube 32 (hereinafter simply referred to as the flow channel 41 of the branch tube 32) is formed in the linear shape in the axial direction (the X-axis direction).

As illustrated in FIGS. 2 and 3, the attachment assist portion 22 holds the second portions 32b of the plurality of branch tubes 32 at a holding portion 22a. In this manner, the attachment assist portion 22 holds the plurality of the tubes 21 that has been integrated. In addition, the attachment assist portion 22 includes a handle 23. Therefore, a worker can attach and detach to and from the circuit unit 11 from the irradiation unit 12 while gripping the handle 23. In this manner, the attachment assist portion 22 functions as assistance that causes the circuit unit 11 to be easily attached to the irradiation unit 12.

The irradiation unit 12 includes an LED arrangement portion 51, the UV LED lamp 52, and a groove portion 53.

A plurality of the LED arrangement portions 51 is formed. As illustrated in FIG. 3, for example, five LED arrangement portions 51 including a first LED arrangement portion 51A to a fifth LED arrangement portion 51E are formed as the plurality of LED arrangement portions 51. Then, the first LED arrangement portion 51A, the second LED arrangement portion 51B, the third LED arrangement portion 51C, the fourth LED arrangement portion 51D, and the fifth LED arrangement portion 51E are formed in this order in the Z-axis direction.

A plurality of the UV LED lamps 52 is provided. The plurality of UV LED lamps 52 is arranged in the X-axis direction and the Y-axis direction in each of the first LED arrangement portion 51A to the fifth LED arrangement portion 51E. Further, the UV LED lamps 52 are arranged only in one row in the Z-axis direction in the first LED arrangement portion 51A and the fifth LED arrangement portion 51E. In addition, the UV LED lamps 52 are arranged in two rows in the Z-axis direction in the second LED arrangement portion 51B, the third LED arrangement portion 51C, and the fourth LED arrangement portion 51D. The UV LED lamp 52 irradiates the blood flowing through the flow channel 41 of the branch tube 32 with UV light in order to inactivate a virus included in the blood. Incidentally, the UV light emitted from the UV LED lamp 52 may be any one of UV-A, UV-B, and UV-C, and particularly, UV-A and UV-B which are hardly reflected or absorbed by erythrocytes are desirably used.

A plurality of the groove portions 53 is formed, and the groove portion 53 is formed between the adjacent LED arrangement portions 51. As a result, a gap is formed between the adjacent LED arrangement portions 51. Further, the holding portion 22a (the second portion 32b of the branch tube 32) of the attachment assist portion 22 in the circuit unit 11 is arranged inside the groove portion 53 (see FIG. 2).

As illustrated in FIG. 3, for example, four groove portions 53 each of which includes a groove portion 53A to a groove portion 53D are formed as the plurality of groove portions 53. The groove portion 53A is provided between the first LED arrangement portion 51A and the second LED arrangement portion 51B, the groove portion 53B is provided between the second LED arrangement portion 51B and the third LED arrangement portion 51C, the groove portion 53C is provided between the third LED arrangement portion 51C and the fourth LED arrangement portion 51D, and the groove portion 53D is formed between the fourth LED arrangement portion 51D and the fifth LED arrangement portion 51E.

In the first LED arrangement portion 51A, the UV LED lamp 52 is arranged in such a direction that the irradiation direction of the UV light becomes the direction of the first groove portion 53A. In addition, in the second LED arrangement portion 51B, the UV LED lamps 52 arranged in two rows in the Z-axis direction are arranged to be directed such that each irradiation direction of the UV light becomes a direction of the first groove portion 53A and a direction of the second groove portion 53B. In addition, in the third LED arrangement portion 51C, the UV LED lamps 52 arranged in two rows in the Z-axis direction are arranged to be directed such that each irradiation direction of the UV light becomes the direction of the second groove portion 53B and a direction of the third groove portion 53C. In addition, in the fourth LED arrangement portion 51D, the UV LED lamps 52 arranged in two rows in the Z-axis direction are arranged to be directed such that each irradiation direction of the UV light becomes the direction of the third groove portion 53C and a direction of the fourth groove portion 53D. Further, in the fifth LED arrangement portion 51E, the UV LED lamps 52 are arranged to be directed such that an irradiation direction of the UV light becomes the direction of the fourth groove portion 53D.

In this manner, when the circuit unit 11 is attached to the irradiation unit 12 from the state illustrated in FIG. 3, the UV LED lamps 52 are arranged at positions on both sides in the Z-axis direction with respect to the flow channel 41 of the branch tube 32 as illustrated in FIG. 1. Further, the plurality of UV LED lamps 52 is arranged along the axial direction (the X-axis direction) of the flow channel 41 of the branch tube 32.

Incidentally, the flow channels 41 of the branch tube 32 are arranged such that two are parallel in the Y-axis direction and four are parallel in the Z-axis direction in the example illustrated in FIG. 1, but the number of the flow channels 41 arranged in parallel is not particularly limited. For example, the flow channels 41 of the branch tube 32 may be arranged such that two or more are arranged in parallel in the Y-axis direction and the Z-axis direction, only one is arranged in the Y-axis direction and two or more are arranged in parallel in the Z-axis direction, or two or more are arranged in parallel in the Y-axis direction and only one is arranged in the Z-axis direction.

In addition, the UV irradiation unit 1 includes a first feed pump 13A and a second feed pump 13B as the feed pump 13. The first feed pump 13A is connected to the inlet-side tube 31. The second feed pump 13B is connected to the outlet-side tube 33.

The control unit 14 is configured using, for example, a microcomputer, and controls an operation of each component of the UV irradiation unit 1 such as drive of the feed pump 13 and irradiation of the UV LED lamp 52.

Next, a description will be given regarding a method of inactivating the virus included in the blood product using the UV irradiation unit 1 as a function of the UV irradiation unit 1 having such a structure.

Figure 4:
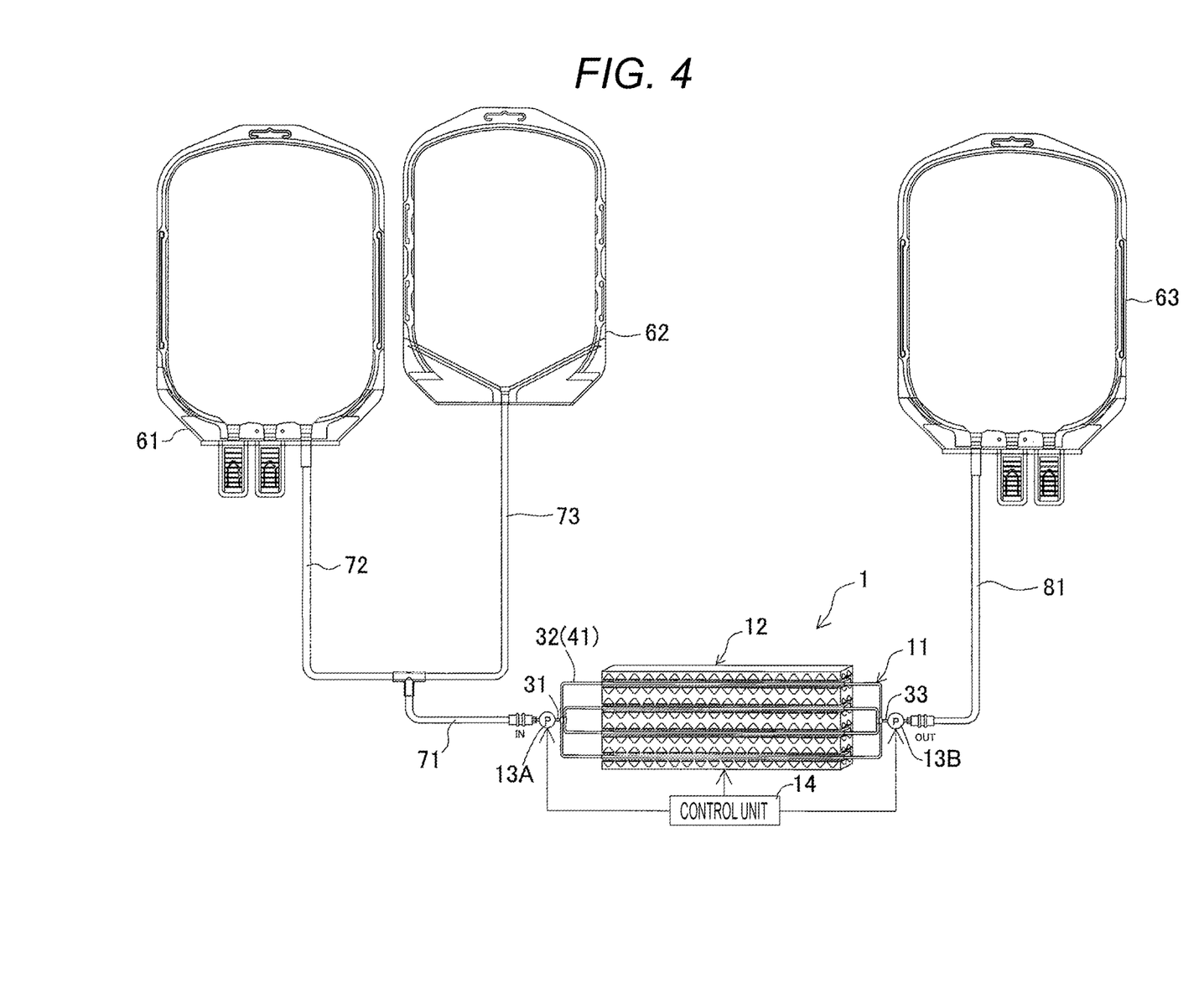
FIG. 4 is a configuration diagram at the time of inactivating a virus included in a blood product using the UV irradiation unit of the present embodiment.

First, a non-inactivated blood product bag 61 containing a blood product prior to inactivation of the virus and a dilute solution bag 62 containing a dilute solution (preserving liquid) are connected to the inlet-side tube 31 of the UV irradiation unit 1 as illustrated in FIG. 4. Specifically, a tube 71 is connected to the inlet-side tube 31 of the UV irradiation unit 1 via the first feed pump 13A. Here, the tube 71 is connected to a tube 72 connected to the non-inactivated blood product bag 61 and a tube 73 connected to the dilute solution bag 62.

In addition, an inactivated blood product bag 63 configured to contain the blood product after virus inactivation is connected to the outlet-side tube 33 of the UV irradiation unit 1 as illustrated in FIG. 4. Specifically, a tube 81 connected to the inactivated blood product bag 63 is connected to the outlet-side tube 33 of the UV irradiation unit 1 via the second feed pump 13B.

Therefore, the control unit 14 drives the first feed pump 13A and the second feed pump 13B so as to cause the blood product to flow from the non-inactivated blood product bag 61 to the circuit unit 11 via the tube 72 and the tube 71. Incidentally, the blood product is diluted with the dilute solution flowing in the circuit unit 11 from the dilute solution bag 62 via the tube 73 and the tube 71 at this time.

Further, the control unit 14 irradiates the blood product flowing through the flow channel 41 of the branch tube 32 with UV light by the UV LED lamp 52. In this manner, the virus included in the blood product is inactivated. Then, the blood product after virus inactivation is contained in the inactivated blood product bag 63. Incidentally, since the concentration of the blood product is lowered by being diluted with the dilute solution, the UV light is hardly absorbed or reflected by erythrocytes, and the processing performance to inactivate the virus is improved. The function of the UV irradiation unit 1 has been described as above.

The plurality of flow channels 41 is arranged in parallel in the UV irradiation unit 1 of the present embodiment as described above. Specifically, the flow channels 41 of the plurality of branch tubes 32 are arranged in parallel in each of the Y-axis direction and the Z-axis direction. In this manner, the multilayer structure in which the plurality of flow channels 41 is arranged in parallel for each of the Y-axis direction and the Z-axis direction is formed in the UV irradiation unit 1.

Here, the UV LED lamp 52 which hardly generates heat is used as a light source for irradiation of UV light in the UV irradiation unit 1, and thus, it is possible to simplify a heat dissipation measure. Thus, the UV LED lamp 52 and the branch tube 32 can be arranged to be close to each other even within a limited space, and can be made multilayered. Therefore, it is possible to increase the volume of the flow channels 41 in the circuit unit 11 by arranging the plurality of branch tubes 32 in parallel to form the multilayer structure in which the plurality of flow channels 41 is arranged in parallel. Thus, it is possible to increase the throughput of blood per unit time in the entire UV irradiation unit 1.

In addition, it is also possible to arrange the UV LED lamps 52 close to each other since the UV LED lamp 52 hardly generates heat so that it is possible to simplify the heat dissipation measure. Therefore, the UV LED lamps 52 are arranged at positions on both the sides in the Z-axis direction with respect to the flow channel 41 of the branch tube 32 in the UV irradiation unit 1 of the present embodiment as illustrated in FIG. 2. In this manner, a double-sided irradiation structure in which the blood flowing through the flow channel 41 is irradiated with UV light from both the sides of the flow channel 41 is formed in the UV irradiation unit 1. Thus, it is possible to increase an irradiation amount of UV light with respect to blood. For example, even when the UV light emitted from the UV LED lamp 52 arranged at a position on one side with respect to the flow channel 41 hits erythrocytes in the blood to be absorbed or reflected, the UV light emitted from the UV LED lamp 52 arranged at a position on the other side of the flow channel 41 can be transmitted into the blood without hitting the erythrocytes in the blood. Thus, the UV light is easily transmitted into the blood.

As described above, the multilayer structure in which the plurality of flow channels 41 is arranged in parallel and the double-sided irradiation structure in which the blood flowing through the flow channel 41 is irradiated with UV light from both the sides of the flow channel 41 are formed in the UV irradiation unit 1 of the present embodiment. Thus, it is possible to increase the irradiation amount of the UV light with respect to the blood while increasing the throughput of blood per unit time, and further, the UV light is easily transmitted into the blood in the UV irradiation unit 1. Therefore, the processing performance to inactivate the virus included in the blood is improved so that it is possible to inactivate the virus included in the blood in a short time according to the UV irradiation unit 1.

In addition, the blood is irradiated with UV light while causing the blood to flow in one direction from the upstream side to the downstream side inside the flow channel 41, thereby inactivating the virus included in the blood in the UV irradiation unit 1 of the present embodiment. Thus, blood stagnation hardly occurs in the UV irradiation unit 1 as compared with a conventional case in which blood contained in a blood bag is irradiated with UV light (in the case of batch-type virus inactivation treatment), and thus, blood coagulation hardly occurs. In particular, the multilayer structure in which the plurality of flow channels 41 is arranged in parallel in the Y-axis direction and the Z-axis direction is formed and the volume of the flow channel 41 is secured in the UV irradiation unit 1. Thus, it is possible to shorten a length of the branch tube 32, that is, a length of the flow channel 41 of the branch tube 32 in the X-axis direction as short as possible. Thus, it is possible to shorten the time to cause the blood to flow through the flow channel 41 as short as possible by making a distance of blood flow in the flow channel 41 as short as possible so that the blood coagulation hardly occurs. Therefore, the blood coagulation hardly occurs, and it is possible to inactivate the virus included in the blood in a short time according to the UV irradiation unit 1.

In addition, according to the UV irradiation unit 1 of the present embodiment, the volume of the flow channel 41 in the circuit unit 11 is secured by arranging the plurality of flow channels 41 having a small flow channel area in parallel instead of securing the volume of the flow channel 41 in the circuit unit 11 by increasing a flow channel area (area of the above-described flow channel section) of the flow channel 41. Here, when the flow channel area of the flow channel 41 is increased, there is a concern that blood coagulation may occur due to generation of a portion where blood stagnates in the flow channel 41. However, since the flow channel area of the flow channel 41 can be made small in the UV irradiation unit 1 of the present embodiment, a portion where blood stagnates in the flow channel 41 is hardly generated, and the blood coagulation hardly occurs.

In addition, it is possible to control a flow rate of the blood flowing through the flow channel 41 by the feed pump 13 according to the UV irradiation unit 1 of the present embodiment, and thus, it is possible to control the flow rate of the blood such that the virus can be efficiently inactivated. In addition, it is also possible to control the flow rate of the blood flowing through the flow channel 41 using the feed pump 13 to a flow rate at which blood coagulation hardly occurs in the flow channel 41.

In addition, a blood product flows with erythrocytes floating inside the flow channel 41 particularly when the blood product of whole blood or concentrated erythrocytes are caused to flow through the flow channel 41 according to the UV irradiation unit 1 of the present embodiment, and thus, the UV light emitted from the UV LED lamp 52 is hardly absorbed or reflected by the erythrocytes. Thus, even when the erythrocytes are included as the blood product of whole blood or concentrated erythrocytes, the UV light is easily transmitted into the blood product, so that the virus included in the blood product is easily inactivated.

In addition, the flow channel section of the flow channel 41 is formed in the flat shape, and the UV LED lamp 52 is arranged at the position in the traverse direction (Z-axis direction) of the flat shape with respect to the flow channel 41. In this manner, it is possible to irradiate a surface formed along the longitudinal direction of the flow channel section of the flow channel 41 with UV light by the UV LED lamp 52. Thus, it is possible to increase the irradiation amount of UV light with respect to the blood flowing through the flow channel 41. In addition, the UV light is easily transmitted into the blood flowing through the flow channel 41.

In addition, the plurality of UV LED lamps 52 is arranged in the axial direction (X-axis direction) of the flow channel 41 of the branch tube 32 in the UV irradiation unit 1 of the present embodiment. In this manner, the UV irradiation unit 1 is formed so as to continuously irradiate the blood flowing through the flow channel 41 along the flow direction thereof. Thus, it is possible to further increase the irradiation amount of UV light with respect to blood.

In addition, the UV LED lamp 52 is less likely to generate heat as compared with a conventional UV lamp such as a mercury UV lamp, and thus, it suffices to simply take the heat dissipation measure. Thus, the UV LED lamp 52 can be brought into close contact with the branch tube 32 as compared with the conventional UV lamp. Therefore, the groove portion 53 in the irradiation unit 12 can be made as small as possible, and thus, it is possible to make the flow channel 41 multilayered within a limited space. Thus, the UV irradiation unit 1 can be miniaturized.

In addition, the life of the UV LED lamp 52 is remarkably increased as compared with the conventional UV lamp. In addition, reduction in illuminance hardly occurs in the UV LED lamp 52. Thus, the performance of processing to inactivate the virus included in the blood hardly varies.

In addition, it is possible to efficiently inactivate the virus included in the blood by adding a photoactive virus inactivating agent such as riboflavin to the blood.

As an example of the UV irradiation unit 1 described above, for example, the illuminance of UV light of the UV LED lamp 52 is set to 30 W, the six flow channels 41 of the branch tube 32 are arranged in the Y-axis direction in five rows in the Z-axis direction, and the length of the flow channel 41 of the branch tube 32 in the axial direction (X-axis direction) is set to 300 mm. As a result, an evaluation result that viruses can be inactivated in 23 minutes for 400 cc of blood, for example, was obtained. Incidentally, when the illuminance of the UV LED lamp 52 was set to 60 W, for example, an evaluation result that viruses can be inactivated in about 12 minutes for 400 cc of blood was obtained.

Figure 5:
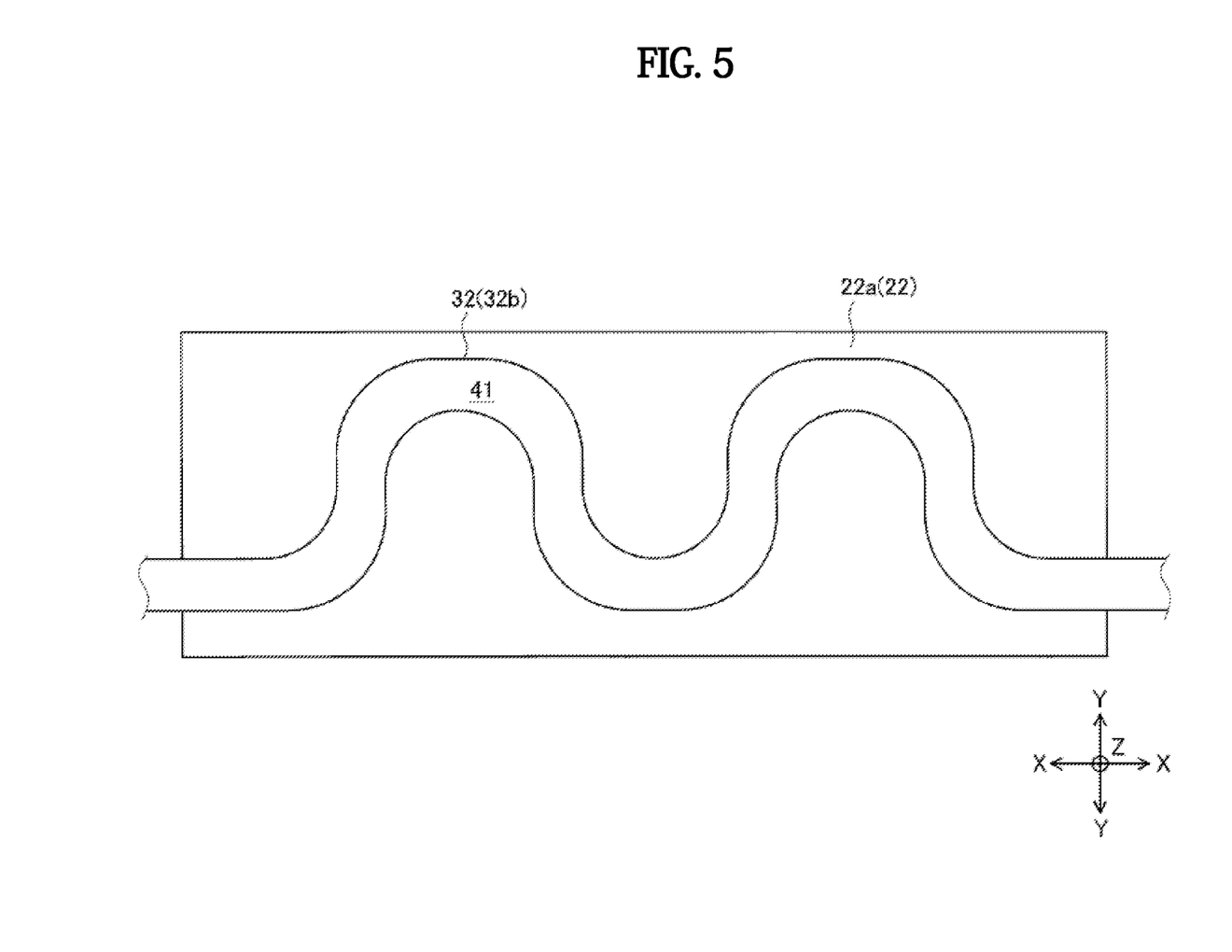
FIG. 5 is a view illustrating a flow channel of a modified example.

In addition, the flow channel 41 of the branch tube 32 may be formed in a curved shape in the axial direction thereof as a modified example. For example, as illustrated in FIG. 5, the flow channel 41 of the branch tube 32 is formed such that the axis thereof is curved from the X-axis direction toward the Y-axis direction and further, is curved from the Y-axis direction toward the X-axis direction. As a result, it is possible to secure the volume of the flow channel 41. Incidentally, even in this modified example, a multilayer structure in which the plurality of flow channels 41 is arranged in parallel in the Z-axis direction is formed, and the UV LED lamps 52 are arranged at positions on both sides with respect to the flow channel 41 in the Z-axis direction. In addition, the plurality of UV LED lamps 52 is arranged in the axial direction of the flow channel 41.

As described above, the UV irradiation unit 1 of the present embodiment includes the flow channel 41 through which blood flows; and the UV LED lamp 52 which irradiates the blood flowing through the flow channel 41 with UV light in order to inactivate the virus included in the blood, in which the multilayer structure in which the plurality of flow channels 41 is arranged in parallel is formed.

Therefore, it is possible to increase the total volume of the flow channels 41 in the circuit unit 11 by forming the multilayer structure in which the plurality of flow channels 41 is arranged in parallel in the UV irradiation unit 1. Thus, it is possible to increase the throughput of the blood per unit time so that the processing performance to inactivate the virus included in the blood is improved. In addition, it is possible to effectively inactivate the virus by the UV light, and thus, the processing performance of inactivating the virus included in the blood is improved. In addition, the blood is irradiated with the UV light while causing the blood to flow through the flow channel 41, the blood stagnation hardly occurs so that the blood coagulation hardly occurs. Thus, the blood coagulation hardly occurs, and it is possible to inactivate the virus included in the blood in a short time according to the UV irradiation unit 1 of the present embodiment.

In addition, the multilayer structure in which the plurality of flow channels 41 is arranged in parallel is formed for each of the Y-axis direction and the Z-axis direction in the UV irradiation unit 1 of the present embodiment. As a result, it is possible to further increase the throughput of blood per unit time. Thus, the processing performance to inactivate viruses included in the blood is further improved so that it is possible to inactivate the virus included in the blood in a shorter time.

In addition, the UV LED lamps 52 are arranged at positions on both sides with respect to the flow channel 41 in the Z-axis direction. As a result, it is possible to increase the irradiation amount of UV light with respect to the blood flowing through the flow channel 41. In addition, the UV light is easily transmitted into the blood flowing through the flow channel 41. Thus, the processing performance to inactivate the virus included in the blood is improved.

In addition, the flow channel section of the flow channel 41 is formed in the flat shape, and the UV LED lamp 52 is arranged at the position in the traverse direction (Z-axis direction) of the flat shape with respect to the flow channel 41 in the UV irradiation unit 1 of the present embodiment. As a result, it is possible to increase the irradiation amount of UV light with respect to the blood flowing through the flow channel 41. In addition, the UV light is easily transmitted into the blood flowing through the flow channel 41. Thus, the processing performance to inactivate the virus included in the blood is improved.

In addition, the plurality of UV LED lamps 52 is arranged in the axial direction of the flow channel 41. As a result, it is possible to increase the irradiation amount of UV light with respect to the blood flowing through the flow channel 41. Thus, the processing performance to inactivate the virus included in the blood is improved.

In addition, the flow channel 41 of the branch tube 32 is formed in a linear shape in the axial direction thereof. As a result, the blood flowing through the flow channel 41 hardly receives a flow channel resistance, and thus, it is possible to increase the throughput of the blood per unit time.

In addition, the flow channel 41 of the branch tube 32 may be formed in a curved shape in the axial direction thereof. As a result, it is possible to secure the volume of the flow channel 41 within a limited space, and thus, it is possible to increase the throughput of the blood per unit time.

Incidentally, it is a matter of course that the above-described embodiments are merely examples and do not limit the present invention, and various improvements and modifications can be made within a scope not departing from a spirit thereof.

The invention claimed is:

1. A light irradiation device comprising:
    a circuit unit comprising
        a plurality of tube holding portions, each of the tube holding portions being in a generally co-planar relationship with the other tube holding portions and each one of the tube holding portions having a plurality of fluid tubes extending there through,
        an inlet tube fluidly connected to an inlet end of each fluid tube of the plurality of fluid tubes,
        an outlet tube fluidly connected to an outlet end of each fluid tube of the plurality of fluid tubes, and
        an attachment assist portion connected to the tube holding portions and supporting the tube holding portions in said generally co-planar relationship,
    and
    an irradiation unit comprising
        a plurality of arrangement portions, each of the arrangement portions being in a generally co-planar relationship with the other arrangement portions and each arrangement portion being separated from an adjacent arrangement portion by a groove, and
a plurality of LED lamps which are mounted in each of the arrangement portions facing one of the grooves formed by adjacent arrangement portions and which irradiate the blood or the blood component flowing through the plurality of tubes with light so as to inactivate a virus included in the blood or the blood component,
wherein the circuit unit may be coupled to the irradiation unit by inserting the tube holding portions into the grooves of the irradiation unit using the attachment assist portion.

2. The light irradiation device according to claim 1, wherein
the fluid tubes are arranged in parallel thereby forming a multilayer structure for each of a first direction orthogonal to an axial direction of the fluid tubes and a second direction orthogonal to the axial direction of the fluid tubes and the first direction.

3. The light irradiation device according to claim 2, wherein
the LED lamps are arranged at positions on both sides with respect to the fluid tubes in a direction orthogonal to the axial direction of the fluid tubes.

4. The light irradiation device according to claim 3, wherein
a section of the fluid tubes perpendicular to the axial direction is formed in a flat shape, and
the LED lamps are arranged at a position on a side in a lateral direction of the flat shape of the fluid tubes.

5. The light irradiation device according to claim 4, wherein
a plurality of the LED lamps is arranged in the axial direction of the fluid tubes.

6. The light irradiation device according to claim 2, wherein
the is fluid tubes are formed in a linear shape in the axial direction of the fluid tubes.

7. The light irradiation device according to claim 2, wherein
the fluid tubes are formed in a curved shape in the axial direction of the fluid tubes.

8. The light irradiation device according to claim 1, wherein the light is ultraviolet light.

9. The light irradiation device according to claim 1, further comprising a handle attached to the attachment assist portion, wherein the tube holding portions are connected to a first side of the attachment assist portion and the handle is attached to a second side of the tube holding portion.

* * * * *